(12) United States Patent
Germain et al.

(10) Patent No.: US 12,402,939 B2
(45) Date of Patent: Sep. 2, 2025

(54) TISSUE RESECTING DEVICE AND METHODS

(71) Applicant: MINERVA SURGICAL, INC., Santa Clara, CA (US)

(72) Inventors: Aaron Germain, Campbell, CA (US); Michael D. Walker, San Francisco, CA (US); Jacob Roland, San Jose, CA (US); Jan Echeverry, San Jose, CA (US)

(73) Assignee: MINERVA SURGICAL, INC., Santa Clara, CA (US)

( * ) Notice: Subject to any disclaimer, the term of this patent is extended or adjusted under 35 U.S.C. 154(b) by 0 days.

(21) Appl. No.: 18/625,790

(22) Filed: Apr. 3, 2024

(65) Prior Publication Data
US 2024/0245450 A1   Jul. 25, 2024

Related U.S. Application Data

(63) Continuation of application No. 17/500,156, filed on Oct. 13, 2021, now Pat. No. 11,957,406, which is a
(Continued)

(51) Int. Cl.
*A61B 18/14* (2006.01)
*A61B 17/32* (2006.01)
(Continued)

(52) U.S. Cl.
CPC .... *A61B 18/1485* (2013.01); *A61B 17/32002* (2013.01); *A61B 2017/320028* (2013.01);
(Continued)

(58) Field of Classification Search
CPC ...... A61B 17/320016; A61B 17/32002; A61B 17/320028; A61B 2017/4216;
(Continued)

(56) References Cited

U.S. PATENT DOCUMENTS

| 4,116,198 A | 9/1978 | Roos |
| 4,706,656 A | 11/1987 | Kuboto |

(Continued)

FOREIGN PATENT DOCUMENTS

| CN | 102596079 A | 7/2012 |
| JP | 2015512659 A | 4/2015 |

(Continued)

OTHER PUBLICATIONS

Medical Applications of Stainless Steel 304, Aug. 30, 2012, AZO Materials, https://www.azom.com/article.aspx?ArticleID=6641.
(Continued)

*Primary Examiner* — Linda C Dvorak
*Assistant Examiner* — Bradford C. Blaise
(74) *Attorney, Agent, or Firm* — Seager, Tufte & Wickhem, LLP

(57) ABSTRACT

Devices, systems, and methods for resecting tissue are disclosed. In some embodiments, a tissue resecting device may comprise an elongated structure having a longitudinal axis, the elongated structure comprising an outer sleeve with a distal window configured to receive uterine polyp tissue and an inner sleeve configured to move between a proximal position and a distal position relative to the window. In some further embodiments, the device may also comprise an electrode element coupled to the inner sleeve. In some even further embodiments, the device may include an insulative layer covering at least a portion of the inner sleeve, wherein the tissue resecting device is configured to fail when used to resect tissue more fibrous than uterine polyp tissue.

20 Claims, 10 Drawing Sheets

Related U.S. Application Data continuation of application No. 15/245,586, filed on Aug. 24, 2016, now abandoned.

(60) Provisional application No. 62/210,540, filed on Aug. 27, 2015.

(51) Int. Cl.
    *A61B 17/42*      (2006.01)
    *A61B 18/00*      (2006.01)
    *A61B 18/16*      (2006.01)

(52) U.S. Cl.
CPC ............... *A61B 2017/4216* (2013.01); *A61B 2018/00083* (2013.01); *A61B 2018/00166* (2013.01); *A61B 2018/00196* (2013.01); *A61B 2018/00202* (2013.01); *A61B 2018/00559* (2013.01); *A61B 2018/00601* (2013.01); *A61B 2018/00982* (2013.01); *A61B 2018/142* (2013.01); *A61B 2018/162* (2013.01); *A61B 2218/002* (2013.01); *A61B 2218/007* (2013.01)

(58) Field of Classification Search
CPC ....... A61B 18/042; A61B 18/12; A61B 18/14; A61B 18/1485; A61B 90/03; A61B 2090/037; A61B 2018/00053; A61B 2018/00083; A61B 2018/00166; A61B 2018/00196; A61B 2018/00202; A61B 2018/00559; A61B 2018/00601; A61B 2018/00982; A61B 2018/1405; A61B 2018/142; A61B 2018/162
See application file for complete search history.

(56) References Cited

U.S. PATENT DOCUMENTS

| | | | |
|---|---|---|---|
| 4,994,026 A | 2/1991 | Fecondini | |
| 4,998,527 A | 3/1991 | Meyer | |
| 5,152,746 A | 10/1992 | Atkinson et al. | |
| 5,176,629 A | 1/1993 | Kullas et al. | |
| 5,312,399 A | 5/1994 | Hakky et al. | |
| 5,382,229 A | 1/1995 | Grabenkort et al. | |
| 5,392,765 A | 2/1995 | Muller | |
| 5,437,629 A | 8/1995 | Goldrath | |
| 5,456,689 A | 10/1995 | Kresch et al. | |
| 5,492,537 A | 2/1996 | Vancaillie | |
| 5,522,805 A | 6/1996 | Vancaillie et al. | |
| 5,556,378 A | 9/1996 | Storz et al. | |
| 5,730,752 A | 3/1998 | Alden et al. | |
| 5,807,240 A | 9/1998 | Muller et al. | |
| 5,814,009 A | 9/1998 | Wheatman | |
| 5,836,909 A | 11/1998 | Cosmescu | |
| 5,868,424 A | 2/1999 | Hamilton et al. | |
| 5,885,277 A | 3/1999 | Korth | |
| 5,906,615 A | 5/1999 | Thompson | |
| 5,921,953 A | 7/1999 | Novak et al. | |
| 5,947,990 A | 9/1999 | Smith | |
| 6,032,673 A | 3/2000 | Savage et al. | |
| 6,039,748 A | 3/2000 | Savage et al. | |
| 6,113,594 A | 9/2000 | Savage | |
| 6,113,597 A | 9/2000 | Eggers et al. | |
| 6,159,160 A | 12/2000 | Hsei et al. | |
| 6,238,366 B1 | 5/2001 | Savage et al. | |
| 6,319,221 B1 | 11/2001 | Savage et al. | |
| 6,979,332 B2 | 12/2005 | Adams | |
| 7,207,966 B2 | 4/2007 | Savare et al. | |
| 7,226,459 B2 | 6/2007 | Cesarini et al. | |
| 7,429,262 B2 | 9/2008 | Woloszko et al. | |
| 7,678,070 B2 | 3/2010 | Kumar et al. | |
| 7,918,822 B2 | 4/2011 | Kumar et al. | |
| 8,061,359 B2 | 11/2011 | Emanuel | |
| 8,062,214 B2 | 11/2011 | Shener et al. | |
| 8,226,549 B2 | 7/2012 | Kumar et al. | |
| 8,308,726 B2 | 11/2012 | Kumar et al. | |
| 8,388,570 B2 | 3/2013 | Kumar et al. | |
| 8,419,626 B2 | 4/2013 | Shener-Irmakoglu et al. | |
| 8,460,178 B2 | 6/2013 | Kumar et al. | |
| 8,512,283 B2 | 8/2013 | Kumar et al. | |
| 8,512,326 B2 | 8/2013 | Shadduck et al. | |
| 8,568,424 B2 | 10/2013 | Shugrue et al. | |
| 8,591,464 B2 | 11/2013 | Kumar et al. | |
| 8,597,228 B2 | 12/2013 | Pyles et al. | |
| 8,652,089 B2 | 2/2014 | Kumar et al. | |
| 8,728,066 B2 | 5/2014 | Shadduck et al. | |
| 8,840,625 B2 | 9/2014 | Adams et al. | |
| 8,840,626 B2 | 9/2014 | Adams et al. | |
| 8,852,085 B2 | 10/2014 | Shener-Irmakoglu et al. | |
| 8,911,363 B2 | 12/2014 | Kumar et al. | |
| 8,951,274 B2 | 2/2015 | Adams et al. | |
| 8,974,448 B2 | 3/2015 | Germain et al. | |
| 9,028,398 B2 | 5/2015 | Kumar et al. | |
| 9,060,760 B2 | 6/2015 | Sullivan et al. | |
| 9,072,431 B2 | 7/2015 | Adams et al. | |
| 9,084,847 B2 | 7/2015 | Klein et al. | |
| 9,095,366 B2 | 8/2015 | Sullivan et al. | |
| 9,155,453 B2 | 10/2015 | Kumar et al. | |
| 9,233,193 B2 | 1/2016 | Truckai et al. | |
| 9,254,142 B2 | 2/2016 | Germain et al. | |
| 9,439,677 B2 | 9/2016 | Germain et al. | |
| 9,439,720 B2 | 9/2016 | Germain et al. | |
| 9,486,233 B2 | 11/2016 | Bek et al. | |
| 9,498,244 B2 | 11/2016 | Orczy-Timko et al. | |
| 9,549,754 B2 | 1/2017 | Shadduck et al. | |
| 2002/0038122 A1 | 3/2002 | Peters | |
| 2008/0249366 A1 | 10/2008 | Gruber et al. | |
| 2009/0270895 A1 | 10/2009 | Churchill et al. | |
| 2009/0270896 A1 | 10/2009 | Sullivan et al. | |
| 2009/0270898 A1 | 10/2009 | Chin et al. | |
| 2011/0160723 A1 | 6/2011 | Tullis et al. | |
| 2012/0078038 A1 | 3/2012 | Sahney et al. | |
| 2012/0101493 A1 | 4/2012 | Masuda et al. | |
| 2013/0046304 A1 | 2/2013 | Germain et al. | |
| 2013/0079702 A1 | 3/2013 | Klein et al. | |
| 2013/0090642 A1 | 4/2013 | Shadduck et al. | |
| 2013/0103021 A1 | 4/2013 | Germain et al. | |
| 2013/0172805 A1 | 7/2013 | Truckai et al. | |
| 2013/0172870 A1 | 7/2013 | Germain et al. | |
| 2013/0231652 A1 | 9/2013 | Germain et al. | |
| 2013/0296847 A1 | 11/2013 | Germain et al. | |
| 2014/0031834 A1 | 1/2014 | Germain et al. | |
| 2014/0100561 A1* | 4/2014 | Biadillah ........... | A61B 18/1492 606/33 |
| 2014/0114300 A1 | 4/2014 | Orczy-Timko et al. | |
| 2014/0221997 A1 | 8/2014 | Shadduck et al. | |
| 2014/0303551 A1 | 10/2014 | Germain et al. | |
| 2014/0324065 A1 | 10/2014 | Bek et al. | |
| 2015/0119795 A1 | 4/2015 | Germain et al. | |
| 2015/0157396 A1 | 6/2015 | Germain et al. | |
| 2015/0216585 A1 | 8/2015 | Kirstgen et al. | |
| 2015/0314048 A1 | 11/2015 | Klein et al. | |
| 2016/0089184 A1 | 3/2016 | Truckai et al. | |
| 2016/0106497 A1 | 4/2016 | Germain et al. | |
| 2016/0317219 A1 | 11/2016 | Germain et al. | |
| 2017/0014180 A1 | 1/2017 | Germain et al. | |
| 2018/0146974 A1 | 5/2018 | Bjursten | |

FOREIGN PATENT DOCUMENTS

| | | |
|---|---|---|
| WO | 2011089769 A1 | 7/2011 |
| WO | 2012178119 A2 | 12/2012 |
| WO | 2013110073 A1 | 7/2013 |

OTHER PUBLICATIONS

International Search Report and Written Opinion dated Nov. 30, 2016 for International Application No. PCT/US2016/048342.

* cited by examiner

TISSUE RESECTING DEVICE AND METHODS

CROSS-REFERENCE TO RELATED APPLICATIONS

This application is a continuation of U.S. application Ser. No. 17/500,156, filed Oct. 13, 2021, now U.S. Pat. No. 11,957,406, which is a continuation of U.S. application Ser. No. 15/245,586, filed Aug. 24, 2016, now abandoned, which application claims priority to U.S. Provisional Patent Application Ser. No. 62/210,540, filed on Aug. 27, 2015, the contents of which are fully incorporated herein by reference.

TECHNICAL FIELD

The present disclosure relates systems and methods for the resection and extraction of tissue, for example, uterine polyps and other abnormal uterine tissue.

BACKGROUND

Uterine polyps are growths attached to the inner wall of the uterus that extend into the uterine cavity. Uterine polyps are usually non-cancerous and can range in size from a few millimeters to a few centimeters. Uterine polyps may cause menorrhagia, bleeding between menstrual periods, reproductive dysfunction, pelvic pressure and pain.

One current treatment of polyps is hysteroscopic resection or myomectomy which involves transcervical access to the uterus with a hysteroscope together with insertion of a resecting instrument through a working channel in the hysteroscope. The resecting instrument may be an electrosurgical resection device such as an RF loop. An electrosurgical resecting device is disclosed in U.S. Pat. No. 5,906,615. In other instances, a mechanical cutter may be used to mechanically cut tissue. Mechanical cutting devices are disclosed in U.S. Pat. Nos. 7,226,459; 6,032,673; 5,730,752; and U.S. Published Patent Appl. 2009/0270898.

SUMMARY

The present disclosure relates systems and methods for resection and extraction of tissue, for example, uterine polyps and other abnormal uterine tissue.

In a first illustrative embodiment, a tissue resecting device for resecting uterine polyps may comprise an elongated structure having a longitudinal axis, the elongated structure comprising an outer sleeve with a distal window configured to receive uterine polyp tissue and an inner sleeve configured to move between a proximal position and a distal position relative to the window and an electrode element coupled to the inner sleeve. In at least some additional embodiments, the device may further include an insulative layer covering at least a portion of the inner sleeve and at least a portion of the electrode element, wherein the tissue resecting device is configured to fail when used to resect tissue more fibrous than uterine polyp tissue.

Another tissue resecting device for resecting uterine polyps comprises an elongated structure having a longitudinal axis. The elongated structure comprises an outer sleeve with a distal window configured to receive uterine polyp tissue and an inner sleeve configured to move between a proximal position and a distal position relative to the window. An electrode element having a first polarity is coupled to the inner sleeve and movable across the window between the proximal position and the distal position. An insulative layer is covering the inner sleeve proximal of the electrode element, wherein a portion of the insulative layer is exposed in the window in the distal position. The insulative layer is configured such that a degree of contact between the insulative layer and the inner sleeve is reduced when used to resect tissue more fibrous than uterine polyp tissue to expose a portion of the inner sleeve to alter an electrical pathway between the electrode element and the outer sleeve serving as a return electrode having a second polarity opposite the first polarity.

Additionally, or alternatively, in any of the above embodiments, the insulative material is configured to delaminate from the inner sleeve when used to resect tissue more fibrous than uterine polyp tissue.

Additionally, or alternatively, in any of the above embodiments, when the tissue resecting device fails, the insulative material may be configured to peel back from the inner sleeve.

Additionally, or alternatively, in any of the above embodiments, the insulative layer may be bonded directly to the electrode element.

Additionally, or alternatively, in any of the above embodiments, the distal window may have a longitudinal length of between about 5 mm and about 10 mm.

Additionally, or alternatively, in any of the above embodiments, the distal window may have a longitudinal length of about 8 mm.

Additionally, or alternatively, in any of the above embodiments, the insulative material may comprise fluorinated ethylenepropylene (FEP).

Additionally, or alternatively, in any of the above embodiments, the inner sleeve may comprise 304 stainless steel.

Additionally, or alternatively, in any of the above embodiments, the outer sleeve may comprise 304 stainless steel.

Additionally, or alternatively, in any of the above embodiments, the insulative layer may have a thickness of between about 0.0127 mm and about 0.038 mm.

Additionally, or alternatively, in any of the above embodiments, the insulative layer may be configured to detach from the electrode component after a predetermined period of activation of the tissue resecting device.

In another embodiment, a tissue resecting device may comprise an elongated assembly comprising concentric outer and inner sleeves extending along an axis, and the inner sleeve may further comprise an electrode element. In some additional embodiments, the device may further include a tissue-receiving window in the outer sleeve and insulative material disposed about at least a portion of the inner sleeve, wherein the insulative material is configured to detach from the inner sleeve when the tissue resecting device is used to resect tissue having a greater fibrosity than uterine polyp tissue.

Additionally, or alternatively, in any of the above embodiments, the electrode element may comprise at least a portion of the inner sleeve.

Additionally, or alternatively, in any of the above embodiments, the insulative material may be attached to the electrode element.

Additionally, or alternatively, in any of the above embodiments, the insulative material may comprise fluorinated ethylenepropylene (FEP).

Additionally, or alternatively, in any of the above embodiments, the insulative material may be configured to detach from the electrode element after a predetermined period of operation of the tissue resecting device.

Additionally, or alternatively, in any of the above embodiments, the tissue-receiving window may have a longitudinal length of between about 5 mm and about 10 mm.

Additionally, or alternatively, in any of the above embodiments, the tissue-receiving window may have a longitudinal length of about 8 mm.

Additionally, or alternatively, in any of the above embodiments, the inner sleeve, the outer sleeve, and the tissue-receiving window may be configured for resecting uterine polyp tissue.

Additionally, or alternatively, in any of the above embodiments, the tissue resecting device may further comprise insulative material disposed along at least a portion of an inner surface of the outer sleeve.

In still another embodiment, a medical device system may comprise an elongated probe comprising: an outer sleeve and an inner sleeve, the outer sleeve including a window disposed proximate a distal end of the outer sleeve, an electrode element disposed proximate a distal end of the inner sleeve, and an insulative layer insulating the inner sleeve from the outer sleeve. In some embodiments, the insulative layer may be configured to peel away from the inner sleeve when the elongated probe is used to resect uterine fibroids. In some additional embodiments, the system may further include a motor for reciprocating the inner sleeve relative to the outer sleeve and an RF generator for delivering energy through the electrode element to resect tissue.

Additionally, or alternatively, in any of the above embodiments, the insulative layer may be attached to at least a portion of the electrode element.

Additionally, or alternatively, in any of the above embodiments, the window may have a longitudinal length of between about 5 mm and about 10 mm.

The above summary of some embodiments is not intended to describe each disclosed embodiment or every implementation of the present disclosure. The Figures, and Detailed Description, which follow, more particularly exemplify these embodiments.

BRIEF DESCRIPTION OF DRAWINGS

The disclosure may be more completely understood in consideration of the following detailed description of various embodiments in connection with the accompanying drawings, in which.

Figure 1:
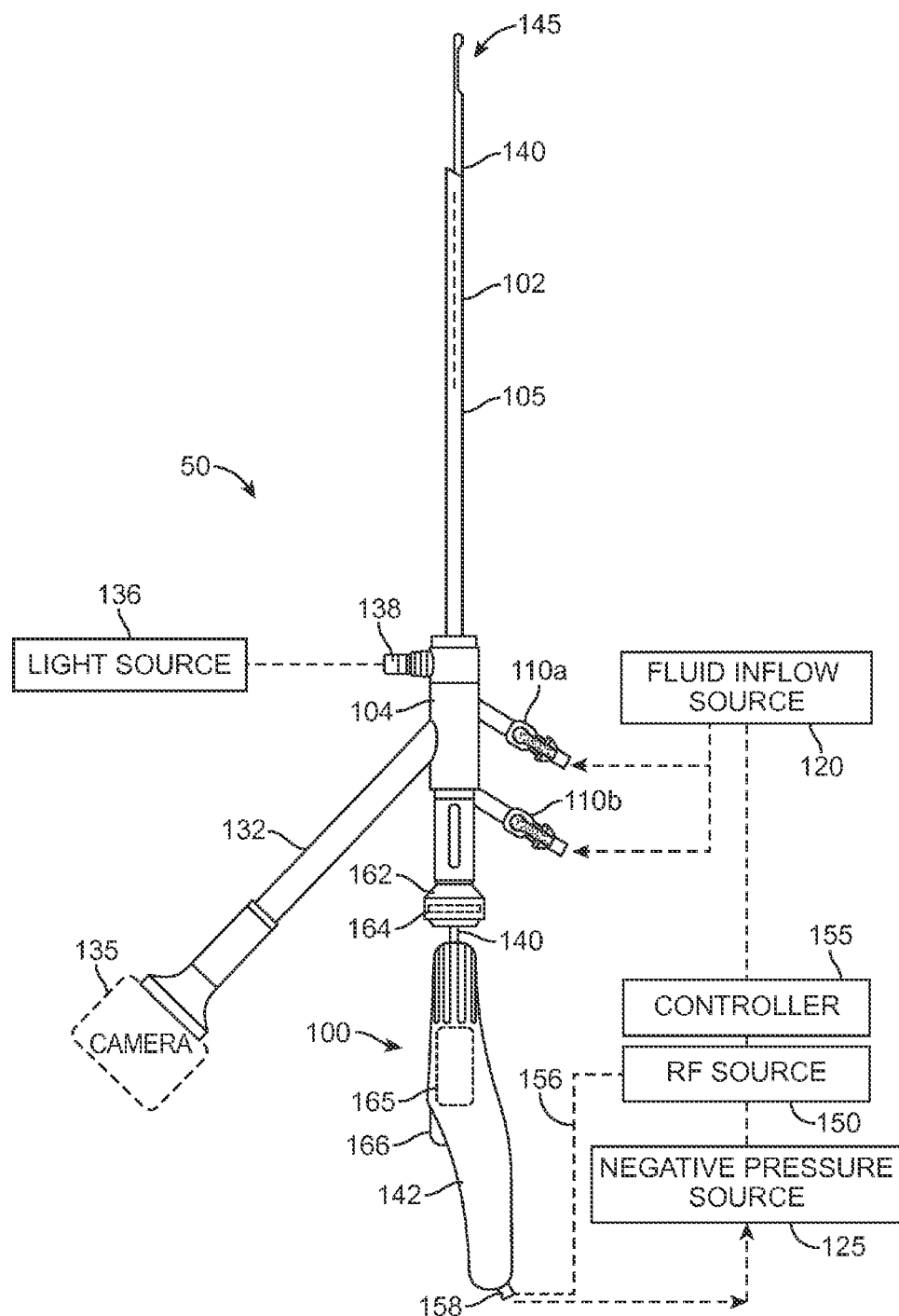
FIG. 1 is a plan view of an assembly including a hysteroscope and a tissue-resecting device inserted through the working channel of the hysteroscope.

While the disclosure is amenable to various modifications and alternative forms, specifics thereof have been shown by way of example in the drawings and will be described in detail. It should be understood, however, that the intention is not to be limited to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

Figure 2:
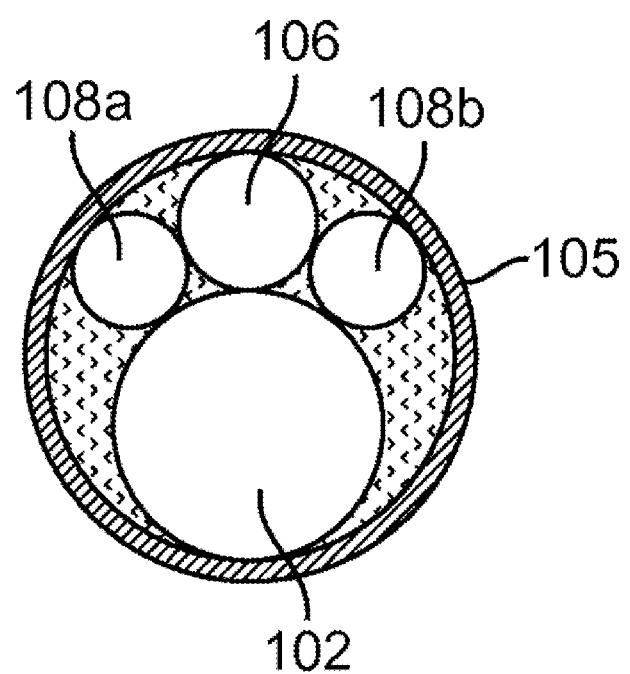
FIG. 2 is a cross sectional view of the shaft of the hysteroscope of FIG. 1.

FIG. 1 illustrates an assembly that comprises an endoscope or hysteroscope 50 used for hysteroscopy together with a tissue-extraction device 100 extending through working channel 102 of hysteroscope 50. Hysteroscope 50 may include handle 104 coupled to elongated shaft 105 having a diameter of 5 mm to 7 mm. Working channel 102 therein may be round, D-shaped or any other suitable shape. Hysteroscope shaft 105 may further be configured with optics channel 106 and one or more fluid inflow/outflow channels 108a, 108b (as seen in FIG. 2). Fluid inflow/outflow channels 108a, 108b may be in fluid communication with valve-connectors 110a, 110b configured for coupling to fluid inflow source 120, or optionally a negative pressure source 125. Fluid inflow source 120 may be a component of a fluid management system which may comprises one or more fluid containers and a pump mechanism which pumps fluid through hysteroscope 50 into the uterine cavity. Handle 104 of hysteroscope 50 may include angled extension portion 132 with optics to which videoscopic camera 135 can be operatively coupled. Light source 136 may also be coupled to light coupling 138 on handle 1004 of hysteroscope 50. Working channel 102 of hysteroscope 50 maybe configured for insertion and manipulation of tissue-resecting and extracting device 100, for example to treat and remove polyp tissue. In some embodiments, hysteroscope shaft 105 may have an axial length of 21 cm, and can comprise a 0° scope, or 15° to 30° scope, for example.

Still referring to FIG. 1, tissue-resecting device 100 may have a highly elongated shaft assembly 140 configured to extend through working channel 102 in hysteroscope 50. Handle 142 of tissue-resecting device 100 may be adapted for manipulating electrosurgical working end 145 of tissue-resecting device 100. In use, handle 142 can be manipulated both rotationally and axially, for example, to orient working end 145 to resect targeted polyp tissue. Tissue-resecting device 100 may have one or more subsystems coupled to handle 142 to enable electrosurgical resecting of targeted tissue. For instance, in some embodiments, radiofrequency generator (RF) source 150 and controller 155 may be coupled to at least one RF electrode carried by working end 145, as described in detail below. In at least some embodiments, electrical cable 156 may be operatively coupled to connector 158 in handle 142. Electrical cable 156 couples RF source 150 to electrosurgical working end 145. Exemplary tissue resection devices are described in U.S. Pat. No. 8,512,326, US 2014/0221997, US 2013/0046304, and US 2014/0114300, each of which is herein incorporated by reference in its entirety.

FIG. 1 further illustrates seal housing 162 that carries flexible seal 164 carried by hysteroscope handle 104 for sealing the shaft 140 of tissue-resecting device 100 in working channel 102 to prevent distending fluid from escaping from a uterine cavity. In some embodiments, as shown in FIG. 1, handle 142 of tissue-resecting device 100 may include motor drive 165 for reciprocating, rotating or otherwise moving a resecting component of electrosurgical working end 145. Handle 142 optionally includes one or more actuator buttons 166 for actuating the tissue-resecting device 100. In other embodiments, a footswitch can be used to operate tissue-resecting device 100. In general, a system including at least hysteroscope 50 and tissue-resecting device 100 may include a switch or control mechanism to provide a plurality of reciprocation speeds, for example 1 Hz, 2 Hz, 3 Hz, 4 Hz and up to 8 Hz. The system may further include a mechanism for moving and locking the reciprocating resecting sleeve in a non-extended position, in an extended position, or in an intermediate position. In some embodiments, the system can further include a mechanism for actuating a single reciprocating stroke.

Figure 3:
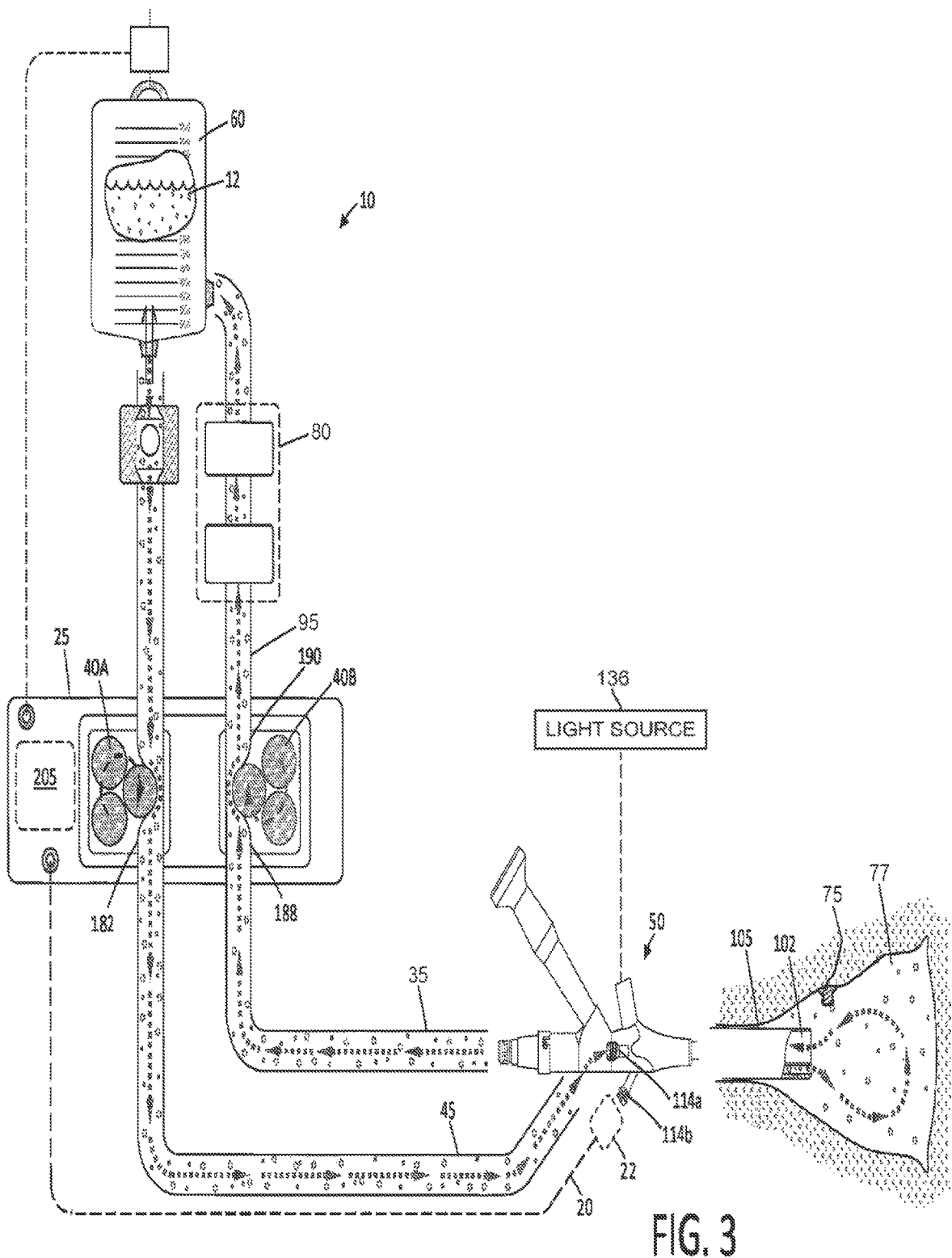
FIG. 3 is a schematic view of a fluid management system that re-circulates distention fluid illustrated in conjunction with a hysteroscope.

FIG. 3 illustrates fluid management system 10 that can be used in conjunction with hysteroscope 50 and tissue-resecting device 100 of FIG. 1. Exemplary closed system fluid management systems are described in US 2013/0172805, US 2013/0079702, US 2014/0303551 and US 2015/0119795, each of which is herein incorporated by reference in its entirety. Referring to FIG. 3, in general, fluid management system 10 may comprise fluid source or reservoir 60 containing distention fluid 12. Controller 25 and two positive displacement (peristaltic) pumps (first infusion pump 40A, second outflow pump 40B) may provide fluid inflows and outflows adapted to maintain distension of the uterine cavity. Filter system 80 may also be included for filtering distention fluid 12 that is removed from the uterine cavity 77 and thereafter returned to fluid reservoir 60. The use of recovered and filtered distention fluid 12 and the replenishment of the volume in fluid reservoir 60 maybe advantageous over open loop systems which do not recover fluid. For instance, closed-loop systems, such as system 10 can effectively measure fluid deficit during a procedure and can provide fluid deficit warnings to insure patient safety. Closed-loop systems may also use only a single bag of distension fluid having a useable volume of about 2500 ml and provide a system lock-out to terminate a procedure after use of a predetermined amount of intravasation of the distension fluid, as determined by measurement of the distension fluid returned to reservoir 60. Closed-loop systems can also reduce procedure cost by reducing the cost of used distension fluid and fluid disposal costs. Further, closed-loop systems can be set up and operated in a more time-efficient manner, and the systems can be more compact and less expensive than current open loop systems.

As illustrated in FIG. 3, fluid management system 10 can include controller 25, which can be either independent of tissue-resection device 100 or configured to operate both fluid management system 10 and tissue-resection device 100 where resection device 100 does not include a motor or controller 155. Controller 25 can be configured to control first and second peristaltic pumps 40A and 40B for providing inflows and outflows of distention fluid 12 from reservoir 60 for the purpose of distending uterine cavity 77 and controlling the intra-cavity pressure during various procedures utilizing hysteroscope 50 and/or tissue-resection device 100.

In some embodiments of FIG. 3, controller 25 may control peristaltic pump 40A to provide positive pressure at the outflow side 182 of the pump to provide inflows of distention fluid 12 through first flow line or inflow line 45 which is in communication with luer fitting 114a and fluid flow channel 108a of hysteroscope 50. Controller 25 may further control second peristaltic pump 40B to provide negative pressure at the inflow side 188 of the pump to second flow line or outflow line 35 to assist in providing outflows of distention fluid 12 from the uterine cavity 77. In operation, second peristaltic pump 40B may also operate to provide positive pressure on outflow side 190 of pump 40B in the second outflow line portion 95 to pump outflows of distention fluid 12 through the filter system 80 and back to fluid reservoir 60.

In some system variations, controller 25 has control algorithms that operate to control pressure in the uterine cavity 77 by pressure signals from a disposable pressure sensor 22 that is coupled to a fitting 114b of hysteroscope 50 which communicates with flow channel 108b that extends through hysteroscope shaft 105 to uterine cavity 77. Pressure sensor 22 can be operatively coupled to controller 25 by cable 20 which sends pressure signals to controller 25. In one embodiment, flow channel 108*b* has a diameter large enough to allow highly accurate sensing of actual intra-cavity pressure. In other devices, the intra-cavity pressure is typically estimated by various calculations using known flow rates through a pump or remote pressure sensors in the fluid inflow line and/or outflow lines that sometimes rely on back pressure calculations. Such fluid management systems are stand-alone systems that are adapted for use with a variety of hysteroscopes. Most such systems are not able to use a pressure sensor that measures actual intra-cavity pressure. Thus, these other devices and fluid management systems rely on algorithms and calculations to estimate intra-cavity pressure, which are typically less accurate than directly sensing intra-uterine pressure.

Fluid channel or sensor channel 108*b* in communication with pressure sensor 22 maybe independent of flow channel 108*a* used for inflows of saline into uterine cavity 77. In the absence of fluid flows in channel 108*b*, for example where another channel of hysteroscope 50 or tissue-resecting device 100 is used for fluid outflows, the fluid in the channel 108*b* then forms a static column of fluid (air or liquid) that transmits changes in pressure to sensor 22 as the pressure in the uterine cavity changes. In one variation, sensor channel 108*b* has a cross-section of at least 1 mm, and fluid pressure within the pressure channel column is equivalent to the pressure in the uterine cavity. Thus, pressure sensor 22 is capable of a direct measurement of pressure within the uterine cavity or other body cavity. In one method, the sensor channel 108*b* can be purged of air by opening a valve (not shown) to release air from channel 108*b* and sensor 22.

FIG. 3 schematically illustrates fluid management system 10 in operation in a diagnostic procedure. Uterine cavity 77 is a potential space and needs to be distended to allow for hysteroscopic viewing. A selected pressure can be set in controller 25, for example via touch screen 205, which the physician knows from experience is suited for distending cavity 77 and/or for performing the diagnostic procedure. In one variation, the selected pressure can be any pressure between 0 and 150 mm Hg. The first peristaltic pump 40A may be operated by controller 25 to operate as a variable speed positive displacement pump that is actuated on demand to provide a flow rate from zero up to 1000 ml/min through inflow line 45. Second peristaltic pump 40B may be operate at a fixed speed to move the saline distention fluid from uterine cavity 77 through outflow line 35. In use, controller 25 and a control algorithm can operate pumps 40A and 40B at selected matching or non-matching speeds to increase, decrease or maintain the volume of distention fluid 12 in uterine cavity 77. Thus, by independent control of the pumping rates of first and second positive displacement pumps 40A and 40B, a selected set pressure in the body cavity can be achieved and maintained in response to signals of actual intra-cavity pressure provided by pressure sensor 22.

In FIG. 3, fluid management system 10 is depicted schematically in conjunction with hysteroscope 50, for example to examine uterine polyp 75. However, fluid management system 10 may further be used with tissue-resecting device 100 to resect polyp 75. For example, tissue-resecting device 100 may be inserted through working channel 102 of hysteroscope 50. In some of these embodiments, outflow line 35 may then be connected to handle 142 of tissue-resecting device 100, and distension fluid 12 may flow out of uterine cavity 77 through a channel of tissue-resecting device 100 and through outflow line 35.

Figure 4:
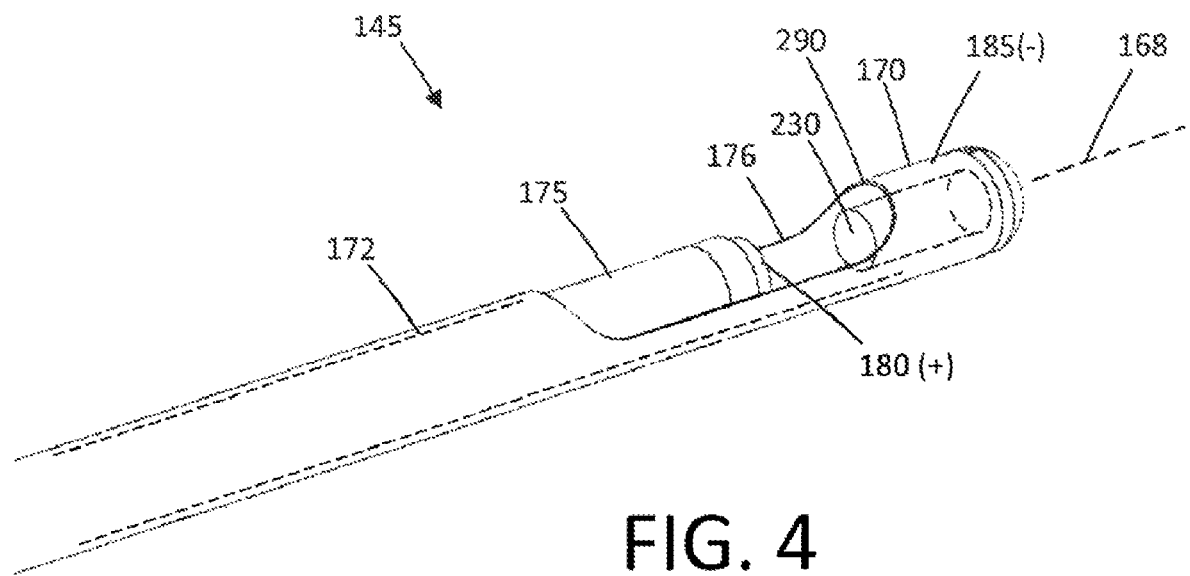
FIG. 4 is a schematic view of the working end of the tissue-resecting device of FIG. 1 showing an outer sleeve in conjunction with an inner sleeve in a partially advanced position.

Referring to FIGS. 1 and 4, electrosurgical tissue-resecting device 100 includes elongate shaft assembly 140 extending about longitudinal axis 168 comprising an exterior or first outer sleeve 170 defining passageway or lumen 172. Lumen 172 may accommodate a second or inner sleeve 175 that can reciprocate (and optionally rotate or oscillate) within lumen 172 to resect tissue. In some embodiments, tissue-receiving window 176 in the outer sleeve 170 has an axial length ranging between about 5 mm to about 10 mm, and in some specific embodiments 8 mm, which may correspond to a size of polyps that tissue-resecting device 100 is designed to remove. In other embodiments, tissue-receiving window 176 may be between about one percent and about three percent of the length of inner sleeve 175 or extraction lumen 160. Tissue-receiving window 176 may extend in a radial angle about outer sleeve 170 from about 45° to about 210° relative to axis 168 of sleeve 170. Outer and inner sleeves 170 and 175 can comprise a thin-wall stainless steel material and function as opposing polarity electrodes as will be described in detail below.

FIG. 6A-7B illustrate insulative layers that may be carried by outer and inner sleeves 170 and 175 to limit, control, and/or prevent unwanted electrical current flows between certain portions of sleeve 170. In some embodiments, outer sleeve 170 may have an O.D. of about 0.143" (3.63 mm) with an I.D. of about 0.133" (3.38 mm). With an inner insulative layer, outer sleeve 170 may have a nominal I.D. of about 0.125" (3.18 mm). In this embodiment, inner sleeve 175 may have an O.D. of about 0.120" (3.05 mm) with an I.D. of about 0.112" (2.84). Inner sleeve 175 with an outer insulative layer may have a nominal O.D. of about 0.123" (3.12) to about 0.124" (3.15 mm) to reciprocate in lumen 172. In general, insulative layers 200 and 202 may have a thickness between about 0.0005" (0.0127 mm) to about 0.0015" (0.038 mm), and in some specific embodiments about 0.001" (0.025 mm). In other embodiments, outer and or inner sleeves 170 and 175 can be fabricated of metal, plastic, ceramic of a combination thereof. The cross-section of the sleeves can be round, oval or any other suitable shape.

In some embodiments, outer sleeve 170 is made from 304 stainless steel, or other lower cost and lower strength biocompatible steels, and may have an O.D. of about 0.140" (3.56 mm) to about 0.143" (3.63 mm) with a wall thickness of about 0.005" (0.13 mm) to about 0.007" (0.18 mm). In these embodiments, inner sleeve 175 may also be made from 304 stainless steel or other suitable lower cost steels. It can be understood that having the largest possible diameter extraction lumen 160 (FIG. 5) may be advantageous, but the diameter of lumen 160 is limited by the O.D. of the shaft assembly, which in turn is limited by the desired cross section of hysteroscope 50. To minimize dilation of the patient's cervix, the maximum scope diameter should be about 0.256" (6.5 mm) which generally may allow for a maximum working channel of about 0.150" (3.81 mm). In some example embodiments, the thin wall tubing and insulation layers may be sized to provide an optimized tissue extraction lumen diameter (given the above scope dimensions and limitations above) that is greater than about 0.090" (2.29 mm) or greater than about 0.100" (2.54 mm)—all accommodated in hysteroscope 50 having an O.D. of about 0.256" (6.5 mm).

Thus, in general, tissue resecting device 100 may comprise an elongated assembly comprising concentric outer and inner sleeves extending along an axis, a tissue-receiving window in the outer sleeve and a reciprocating inner sleeve having an extraction lumen 160. Additionally, the ratio of the diameter of extraction lumen 160 to the outer diameter of outer sleeve 170 is at least about 0.65:1 to about 0.70:1.

In another aspect, the diameter of extraction lumen 160 to the outer diameter of hysteroscope 50 is at least about 0.35:1 to about 0.40:1.

As can be seen in FIG. 4, a distal end of inner sleeve 175 may comprises a first polarity electrode with distal resecting electrode edge 180(+) about which plasma can be generated. Electrode edge 180(+) also can be described as an active electrode during tissue resecting since electrode edge 180(+) then has a substantially smaller surface area than the opposing polarity or return electrode. In some embodiments, as in FIG. 4, the exposed surfaces of outer sleeve 170 may comprise second polarity electrode 185(−), which thus can be described as the return electrode since during use electrode 185(−) has a substantially larger surface area compared to the functionally exposed surface area of the active electrode edge 180(+).

Figure 5:
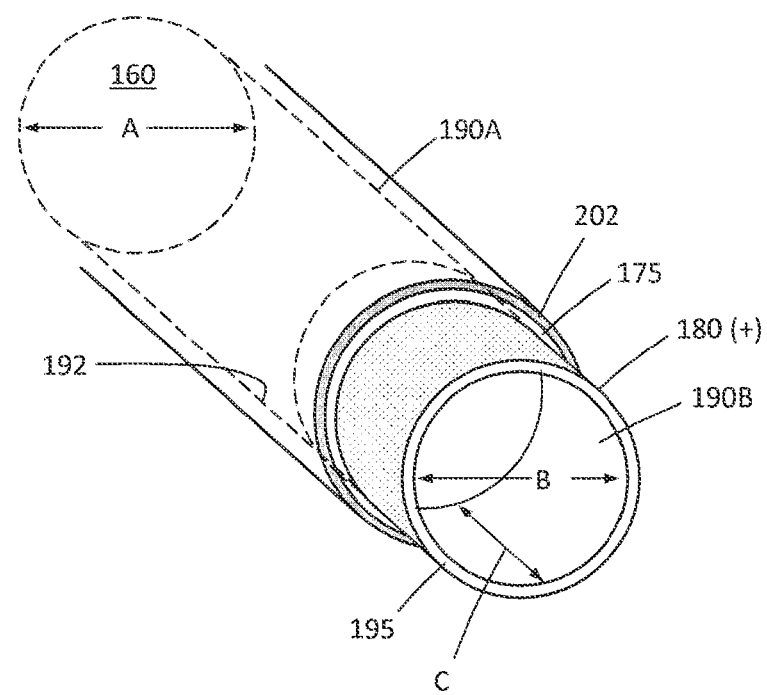
FIG. 5 is a schematic perspective view of the working end of the inner sleeve of FIG. 4.
Figure 6A:
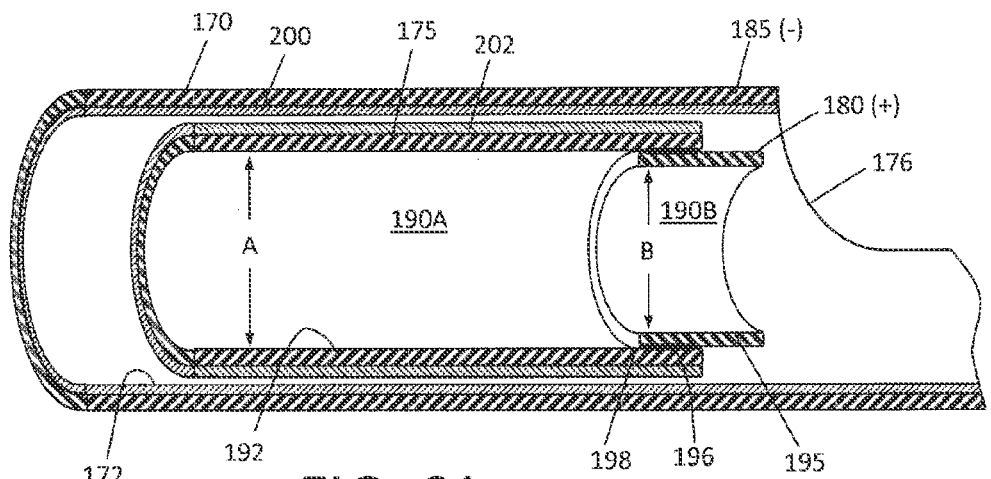
FIG. 6A is a schematic cut-away view of a portion of the outer sleeve and the inner sleeve of FIG. 4.

As described, inner sleeve or resecting sleeve 175 may have an interior tissue extraction lumen 160 with first and second interior diameters that are adapted to electrosurgically resect tissue volumes rapidly and consistently extract the resected tissue strips through elongated lumen 160 without clogging. Referring now to FIGS. 5 and 6A, it can be seen that inner sleeve 175 may have a first portion 190A having a first diameter as indicated at A. First portion 190A may extend from handle 142 (FIG. 1) to distal region 192 of sleeve 175 where tissue extraction lumen 160 transitions to a second portion 190B with a reduced diameter indicated at B. The diameter of second portion 190B is defined by electrode sleeve element 195 that provides resecting electrode edge 180. The axial length C of the second portion 190B can range from about 1 mm to about 15 mm. In some embodiments, the first diameter A is about 0.106" (2.69 mm) and the second reduced diameter B is about 0.095" (2.41 mm) and has an axial length of about 2 mm. The cross-sectional area of second portion 190B may be less than 95% of cross-sectional area of first portion 190A, or less than 90% of the cross-sectional area of first portion 190A, or 85%, or 80% in other embodiments. As shown in FIG. 5, inner sleeve 175 can be an electrically conductive stainless steel, and second portion 190B can also comprise stainless steel electrode sleeve element 195 that is welded in place by weld 196 (FIG. 6A). In other alternative embodiments, inner sleeve 175 and electrode sleeve element 195 can comprise a tungsten tube that can be press fit into distal end 198 of inner sleeve 175.

FIGS. 5 and 6A further illustrate the interfacing insulation layers 202 and 204 that may be carried by first and second sleeves 170, 175, respectively. In FIG. 6A, outer sleeve 170 is lined with a thin-wall insulative material 200, such as perflouroalkoxy alkane (PFA), or other polymeric materials. Similarly, inner sleeve 175 may have an exterior insulative layer 202. These insulative layers can be lubricious as well as electrically insulative to reduce friction during reciprocation of inner sleeve 175. Insulative layers 200 and 202 can comprise a lubricious, hydrophobic or hydrophilic polymeric material. For example, the material can comprise a bio-compatible material such as TEFLON®, polytetrafluoroethylene (PTFE), fluorinated ethylenepropylene (FEP), polyethylene, polyamide, ECTFE (Ethylenechlorotrifluoroethylene), ETFE, PVDF, polyvinyl chloride, silicone, or the like.

Figure 6B:
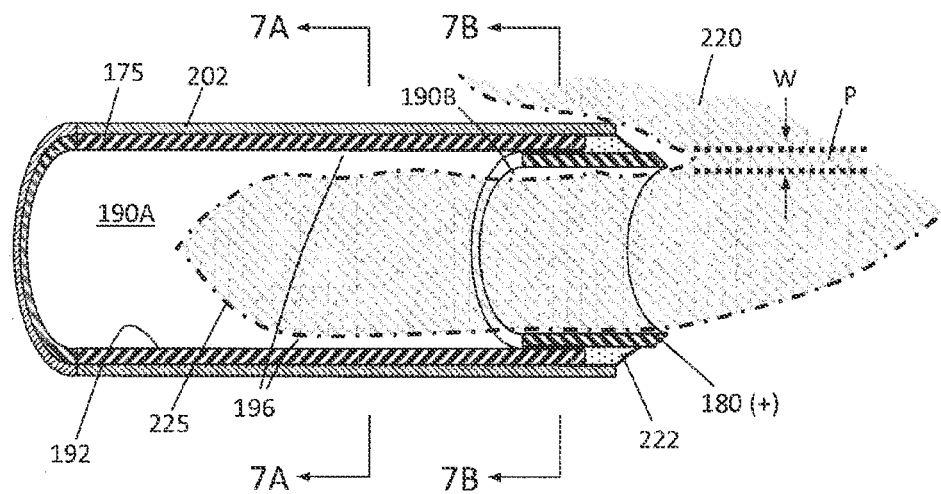
FIG. 6B is a another schematic cut-away view of a portion of the outer sleeve and the inner sleeve of FIG. 4 including tissue received within a lumen of the inner sleeve.

Turning to FIG. 6B, another variation of inner sleeve 175 is illustrated in a schematic view together with a tissue volume being resected with plasma electrode edge 180. In this embodiment, as in other embodiments, an RF source operates at selected operational parameters to create a plasma around electrode edge 180 of electrode sleeve element 195. The plasma generated at electrode edge 180 can resect and ablate a path P in tissue 220, as tissue resecting device 100 is movable relative to tissue 220 or inner sleeve 175 is moved relative to outer sleeve 170, and is suited for resecting uterine polyp tissue and other abnormal uterine tissue. As seen in FIG. 6B, the distal portion of resecting sleeve 175 may include ceramic collar 222 adjacent to electrode sleeve element 195. In these embodiments, insulative layer 202 may extend over inner sleeve 175, but may not contact electrode sleeve element 195. In these embodiments, insulative layer 202 may instead be attached to ceramic collar 222. Ceramic collar 222 collar may function to confine plasma formation about distal electrode edge 180 and help to prevent plasma from contacting and damaging polymer insulative layer 202 on resecting sleeve 175 during operation.

Figure 7A:
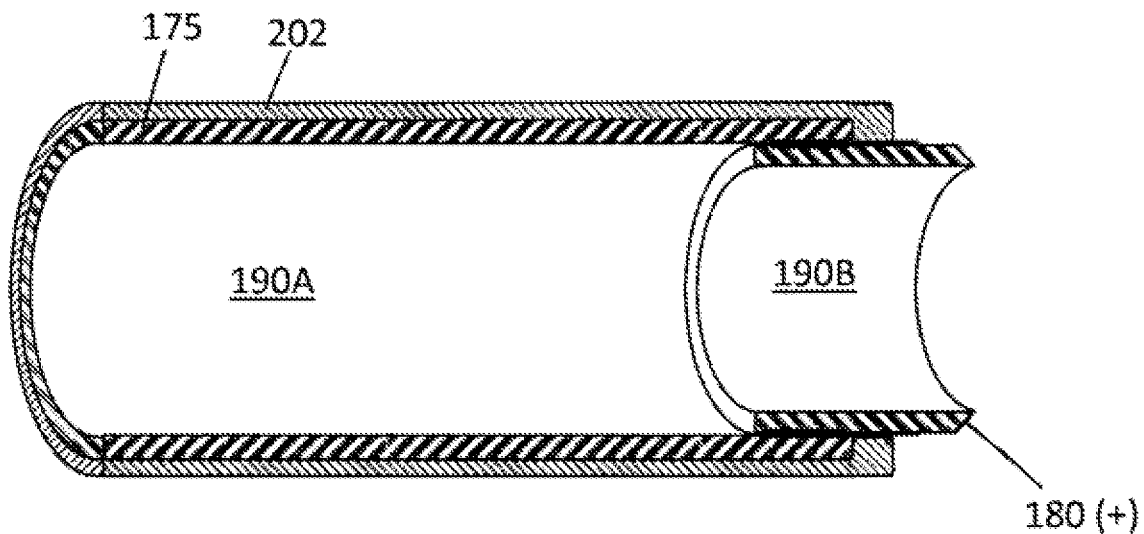
FIG. 7A is a schematic cut-away view of a portion of the inner sleeve of FIG. 4 including an insulative layer.

However, in other embodiments, as depicted in FIG. 7A, tissue-resecting device 100 may not include ceramic collar 222. In these embodiments, insulative layer 202 may extend distally beyond a distal end of inner sleeve 175 and cover at least a portion of electrode sleeve element 195. For instance, insulative layer 202 may be bonded directly to electrode sleeve element 195. Without a ceramic collar, the plasma generated at electrode edge 180(+) during resection may wear down insulative layer 202 more quickly than if a ceramic collar had been included between electrode sleeve element 195 and insulative layer 202. In some additional embodiments, insulative layer 202 may be comprised of a material that may be less wear-resistant or degrade relatively more easily than other materials. For instance, insulative layer 202 may comprise FEP, as opposed to a polyester material.

In some embodiments, tissue-resecting device 100 may be configured to be used only for particular procedures, such as for resecting uterine polyps, or used for a particular number of procedures. For instance, uterine polyps may be generally less fibrous or mechanically rigid than uterine fibroids. Accordingly, the materials of tissue-resecting device 100 configured for uterine polyp resection may not need to be as highly wear-resistant or stand up to a higher level of forces that may be present during resection of uterine fibroids. Utilizing less-wear resistant materials and/or weaker materials may allow tissue-resecting device to be built for a lower cost than devices configured for resection of uterine fibroids. For example, inner and outer sleeves 170, 175 may be comprised of 304 stainless steel or another lower strength bio-compatible stainless steel. Additionally, at least insulative layer 202 may be comprised of FEP as opposed to more durable materials, such as polyesters or other polymers.

Figure 7B:
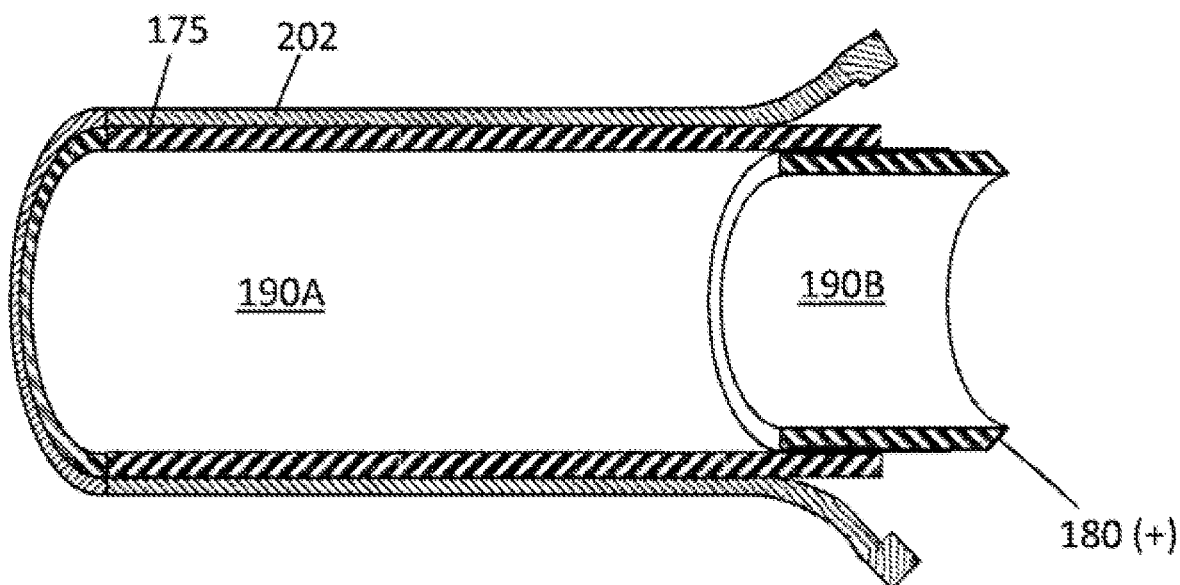
FIG. 7B is a schematic cut-away view of a portion of the inner sleeve of FIG. 4 including the insulative layer peeling away from the inner sleeve.

In these embodiments, insulative layer 202 may be configured to peel back from electrode sleeve element 195 and/or inner sleeve 175, as depicted in FIG. 7B, after a duration of time of using the device 100, a particular number of activations of tissue-resection device 100 or after a particular total length of activation. In additional or alternative embodiments, insulative layer 202 may be configured to peel back from electrode sleeve element 195 and/or inner sleeve 175 when tissue-resection device 100 is used for procedures imparting a greater amount of force on tissue-resection device 100 than during resection of uterine polyps, such as where tissue-resection device 100 is used to resect uterine fibroids or other abnormal tissue that is more fibrous than uterine polyps. Activation of tissue-resection device 100 may include providing RF energy through electrode sleeve element 195 and/or reciprocation of inner sleeve 175 relative to outer sleeve 170. Once insulative layer 202 peels back or otherwise becomes detached from inner sleeve 175, the normal flow pathway of the RF energy may change, resulting in tissue-resecting device 100 becoming non-operational. In this manner, tissue-resection device 100 may be configured to fail or stop working under conditions different from those for which tissue-resection device 100 was designed. For example, the portion of insulative layer 202 exposed in the window 176 of outer sleeve 170 as the inner sleeve 175 moves to the distally extended position (distal or window-closed position) may wear or become delaminated from the inner sleeve 175 through repeated frictional contact with tissue during reciprocation of the inner sleeve 175 relative to the outer sleeve 170 (thus reducing the degree of contact between the insulative layer 202 and the inner sleeve 175), which may expose a portion of the inner sleeve 175 causing a modified or altered electrical pathway between a now exposed electrically conductive portion of the inner sleeve 175 and the exposed electrically conductive portion of the outer sleeve 170 serving as the return electrode. Such modification of the electrical pathway may cause an electrical short or impedance change, making the device 100 non-operational.

Referring back to FIG. 6B, in some aspects, the path P formed in tissue 220 with the plasma at electrode edge 180 may provide a path P having an ablated width indicated at W, where such path width W is substantially created due to tissue vaporization. This removal and vaporization of tissue in path P is different than the effect of cutting similar tissue with a sharp blade edge, as in various prior art devices. A sharp blade edge can divide tissue (without cauterization) but applies mechanical force to the tissue and may prevent a large cross section slug of tissue from being cut. In contrast, the plasma at the electrode edge 180 can vaporize a path P in tissue without applying any substantial force on the tissue to thus resect larger cross-sections of strips of tissue. Further, the plasma resecting effect reduces the cross section of tissue strip 225 received in the tissue-extraction lumen of second portion 190B. FIG. 6B depicts tissue strip 225 entering the lumen of second portion 190B which has a smaller cross-section than the lumen of second portion 190B due to the vaporization of tissue. Further, the cross section of tissue 225 as it enters the larger cross-section lumen of first portion 190A results in even greater free space 196 around the tissue strip 225. Thus, the resection of tissue with plasma electrode edge 180, together with the lumen transition from the smaller cross-section of second portion 190B to the larger cross-section of first portion 190A of tissue-extraction lumen 160 can significantly reduce or eliminate the potential for successive resected tissue strips 225 to clog lumen 160. Prior art resection devices with smaller diameter tissue-extraction lumens typically have problems with tissue clogging.

In other aspects where a system includes a negative pressure source coupled to the proximal end of tissue-extraction lumen 160, the negative pressure source may also assists in aspirating and moving tissue strips 225 in the proximal direction to a collection reservoir (not shown) outside handle 142 of the device.

Figure 8A:
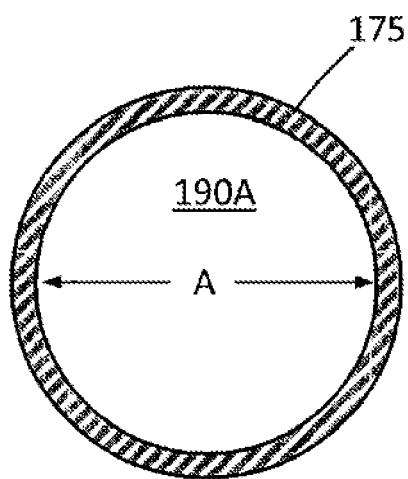
FIG. 8A is a cross-sectional view of the inner sleeve of FIG. 6B taken along line 7A-7A.
Figure 8B:
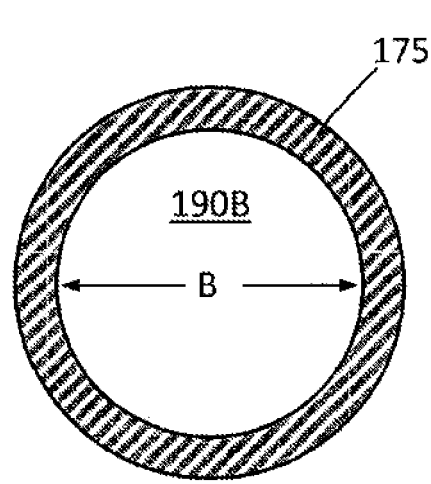
FIG. 8B is a cross-sectional view of the inner sleeve of FIG. 6B taken along line 7B-7B.
Figure 9:
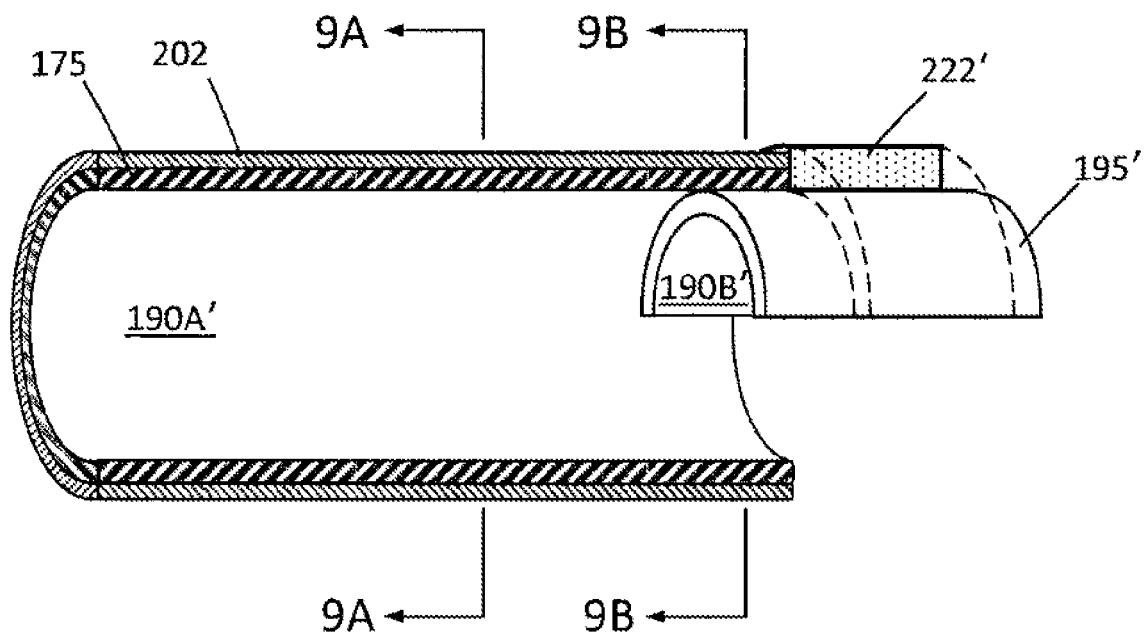
FIG. 9 is schematic view of a distal portion of another embodiment of the inner sleeve.
Figure 10A:
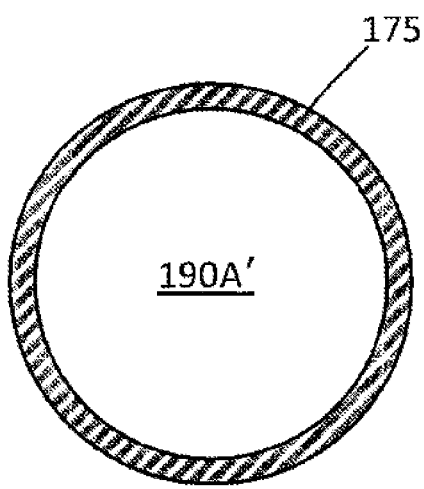
FIG. 10A is a cross-sectional view of the inner sleeve of FIG. 9 taken along line 9A-9A.
Figure 10B:
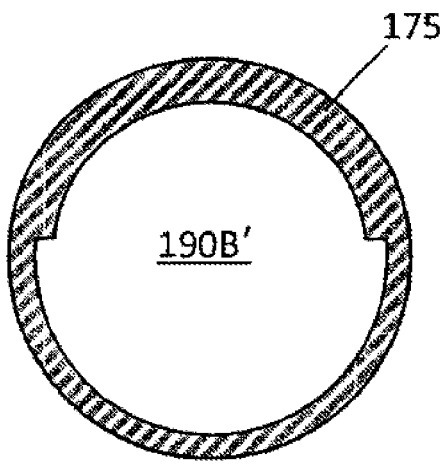
FIG. 10B is a cross-sectional view of the inner sleeve of FIG. 9 taken along line 9B-9B.

FIGS. 8A-8B illustrate the change in lumen diameter 160 of resecting sleeve 175' of FIG. 6B. FIG. 9 illustrates the distal end of a variation of resecting sleeve 175' which is configured with electrode sleeve element 195' that is partially tubular in contrast to the previously described tubular electrode sleeve element 195 (FIGS. 5 and 6A). FIGS. 10A-10B again illustrate the change in cross-section of tissue-extraction lumen 160 between second portion 190B' having a reduced cross-section and first portion 190A' having an increased cross-section region 190A' in relation to resecting sleeve 175' of FIG. 9. Thus, the functionality remains the same whether electrode sleeve element 195' is tubular or partly tubular. In FIG. 9, ceramic collar 222' is shown, in one variation, as extending only partially around sleeve 175' to cooperate with the radial angle of electrode sleeve element 195'. Further, the variation of FIG. 9 illustrates that ceramic collar 222' has a larger outside diameter than insulative layer 202. Thus, friction may be reduced since the short axial length of ceramic collar 222' interfaces and slides against interfacing insulative layer 200 about the inner surface of lumen 172 of outer sleeve 170. However, in other embodiments, resecting sleeve 175' may not include ceramic collar 222', as described with respect to sleeve 175.

In some aspects, the axial length of tissue-extraction lumen 160 may range between from about 17.7" (450 mm) to about 21.7" (550 mm) for access to a uterine cavity. In some embodiments, shaft assembly 140 of tissue-resecting device 100 may be about 35 cm in length. However, in other embodiments, shaft assembly 140 include tissue-extraction lumen 160 that is at least about 10 cm, about 20 cm, about 30 cm, or about 40 cm in length.

Figure 11:
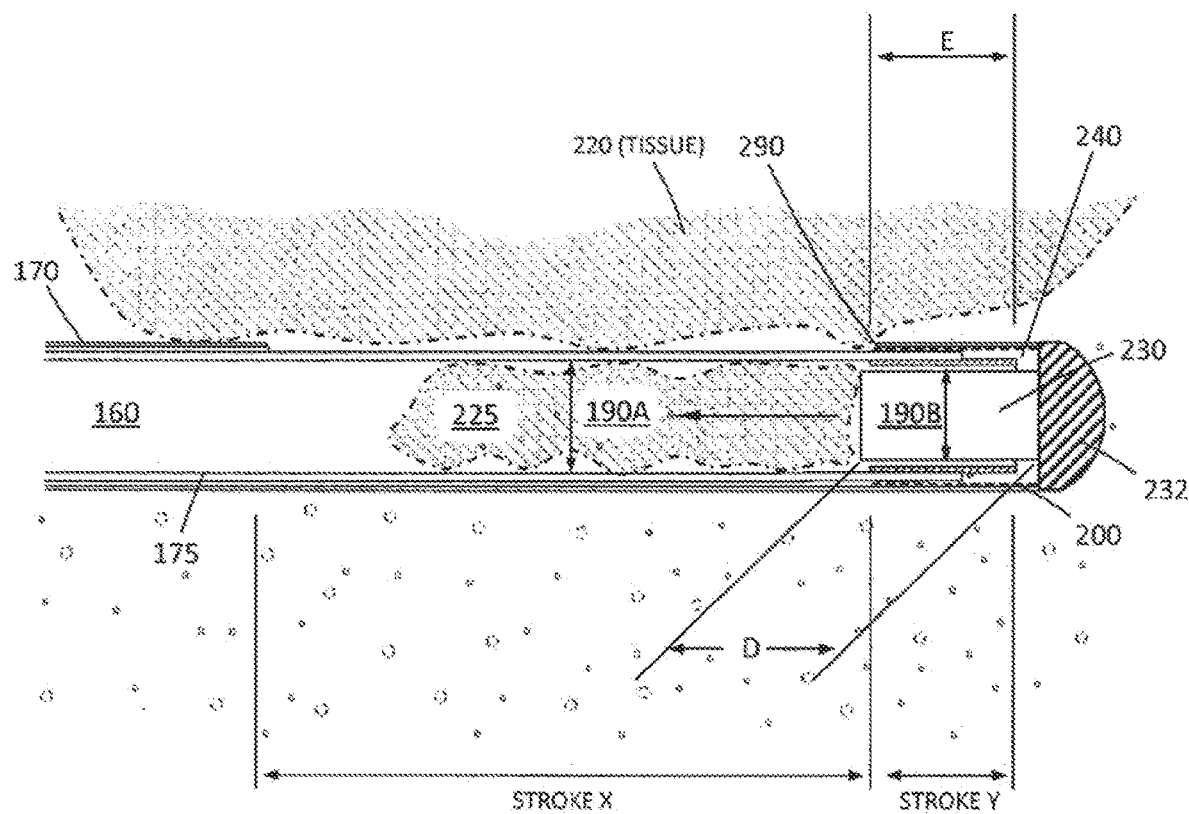
FIG. 11 is an enlarged sectional view of a working end with an inner sleeve in a fully advanced position illustrating a tissue displacement member.

Now referring to FIG. 4 and FIG. 11, one aspect of the disclosure comprises a "tissue displacement" mechanism that is configured to displace and move tissue strips 225 in the proximal direction in lumen 160 of inner sleeve 175 to ensure that tissue 225 does not clog lumen 160. As can be seen in FIG. 4 and FIG. 11, one tissue displacement mechanism comprises projecting element 230 that extends proximally from distal tip or body 232 that is fixedly attached to outer sleeve 170. Projecting element 230 may extend proximally along central axis 168 in a distal chamber 240 defined by outer sleeve 170 and the interior surface of distal tip 232. In some embodiments, as depicted in FIGS. 4 and 11, shaft-like projecting element 230 thus may function as a plunger or pushing member and can push captured tissue strip 225 in the proximal direction from the lumen of second portion 190B of inner sleeve 175 as sleeve 175 moves to its fully advanced or extended position (FIG. 11). For this reason, the length D of projecting element 230 may be at least as great as the axial length E of the second portion 190B of inner sleeve 175. Further, as depicted in FIG. 11, the stroke Y of inner sleeve 175 extends at least about 3 mm, 4 mm, or 5 mm distally beyond the distal edge of window 290. In another aspect, the stroke Y of inner sleeve 175 may be at least 5% or 10% of the total stroke of inner sleeve 175 (stroke X+stroke Y in FIG. 11).

In general, displacement feature or projecting element 230 may have a maximum cross-section that extends substantially across a cross-section of extraction lumen 160. In some variations, displacement feature 230 may have a cross-sectional area that substantially occupies the cross-sectional area of second portion 190B of inner sleeve 175. FIGS. 4 and 11 illustrate projecting element 230 as cylindrical. However, in other embodiments projecting element 230 may be shaped differently. For instance, projecting element 230 may have a symmetric shape relative to a central axis of extraction lumen 160, and may be star-shaped or fluted with ribs and channels to allow distension fluid to flow therethrough. In other embodiments, projecting element 230 can have an asymmetric cross sectional shape with any number or flutes, grooves, lumens or bore extending about its axis. In at least some embodiments, projecting element 230 may be comprised of a dielectric material such as a ceramic or polymer.

In some aspects, the tissue resecting device may comprise an elongated assembly comprising concentric outer and inner sleeves, with a tissue-receiving window in the outer sleeve open to an interior lumen with a distal lumen portion extending distal to the window. The inner sleeve may further be configured with a first axially-extending channel having a greater cross-sectional area and a second axially-extending channel portion having a second smaller cross-sectional area and wherein the ratio of lengths of the distal lumen portion relative to the first channel at least 1:1. In some embodiments, the device may be configured with a length of the distal lumen portion that is at least 5 mm. In these embodiments, the length of the first axially-extending channel may be at least 5 mm. In other embodiments, the ratio of lengths of the distal lumen portion relative to the diameter of the interior lumen is at least 1:1. In still other embodiments, the ratio is at least 1.5:1. In these embodiments, the length of the distal lumen portion may be at least 5 mm. In other variations, the diameter of the interior lumen is less than 5 mm.

In other aspects, a tissue resecting device may comprise a handle coupled to an elongated tubular assembly comprising outer and inner concentric sleeves and a tissue-receiving window in the outer sleeve communicating with an interior passage-way extending through the assembly. In some of these embodiments, a distal edge of the window may be spaced at least 4 mm, 6 mm, 8 mm, or 10 mm from the distal end of the interior passageway. In these variations, the mean cross-section of the passageway may be less than 5 mm, 4 mm, or 3 mm.

Some embodiments of a tissue resecting device comprise a handle coupled to an axially-extending shaft assembly defining a tissue-receiving window communicating with an interior extraction lumen for extracting tissue. The shaft assembly may comprise axially-extending first and second elements with at least one element axially moveable relative to the other element between a first position and a second position, and a displacement feature configured to displace resected tissue from the extraction lumen. In these embodiments, the first position may comprise an open-window configuration for receiving tissue therein and the second position is a closed-window configuration. The movement of the elements from the first position toward the second position resects tissue with an edge of one of the elements. The edge may comprise an RF electrode edge. The displacement feature (FIG. 4 and FIG. 11) or projecting element 230 can be coupled to the first element and can project axially relative to an axis of the extraction lumen. These embodiments may be configured with an extraction lumen having first and second cross-sectional areas, wherein a distal region of the extraction lumen has a first lesser cross-sectional area and a medial portion of the extraction lumen has a second greater cross-sectional area. In some variations, the distal region of the extraction lumen may have the first cross-sectional area extends axially at least 2 mm, 4 mm, 6 mm, or 8 mm. In other variations, the displacement feature may be configured to extend axially into the extraction lumen in the second closed-window configuration at least 2 mm, 4 mm, 6 mm, or 8 mm.

Some methods of resecting tissue may comprise resecting tissue with a reciprocating sleeve having an extending stroke and a retracting stroke within an outer sleeve, wherein the extending stroke resects and captures tissue received by a tissue-receiving window in the outer sleeve. The method may further comprise pushing the captured tissue in the proximal direction in the inner sleeve with a displacement member when the inner sleeve is in a transition range in which the inner sleeve transitions from the extending stroke to the retracting stroke. Further, the displacement member may be configured to push the captured tissue at least in part from a second portion of the inner sleeve having a smaller cross-section lumen to a first portion of the inner sleeve having a larger cross-section lumen. Thereafter, the negative pressure source can more effectively extract and aspirate the tissue from the lumen.

In some variations, the resecting step can include applying RF current to generate plasma at an electrode edge 180 on inner sleeve 175 and further comprising the step of terminating RF current at the distal end of the first resecting stroke. Alternatively, the system and controller 155 can terminate RF current during the second resecting stroke. Alternatively, the controller 155 can terminate RF current during the retracting stroke.

In a further variation, the controller can apply RF current to the electrodes during at least a portion of the retracting stroke to thereby cauterize adjacent tissue. The cautery effect can be provided during the retracting stroke at the same operational parameters as used during the first resecting stroke, or at different operational RF parameters than used during the first resecting stroke.

Those skilled in the art will recognize that the present disclosure may be manifested in a variety of forms other than the specific embodiments described and contemplated herein. Specifically, the various features described with respect to the various embodiments and figures should not be construed to be applicable to only those embodiments and/or figures. Rather, each described feature may be combined with any other feature in various contemplated embodiments, either with or without any of the other features described in conjunction with those features. Accordingly, departure in form and detail may be made without departing from the scope of the present disclosure as described in the appended claims.

What is claimed:

1. A tissue resecting device comprising:
   an elongated structure having a longitudinal axis, the elongated structure comprising an outer sleeve with a distal window configured to receive tissue and an inner sleeve configured to move between a proximal position and a distal position relative to the window;
   an electrode element coupled to the inner sleeve and extending distally of the inner sleeve, wherein the electrode element is distinct from the inner sleeve; and
   an insulative layer disposed on an outer surface of the inner sleeve and extending uninterrupted onto an outer surface of the electrode element, wherein the outer surface of the electrode element extends distal of the insulative layer;
   wherein the electrode element serves as an active electrode having a first polarity and the outer sleeve serves as a return electrode having a second polarity opposite the first polarity.

2. The tissue resecting device of claim 1, wherein the insulative layer is bonded directly to the outer surface of the electrode element.

3. The tissue resecting device of claim 1, wherein the insulative layer is configured to wear away or delaminate from the outer surface of the electrode element after a predetermined duration of time of using the tissue resecting device.

4. The tissue resecting device of claim 1, wherein the insulative layer is configured to wear away or delaminate from the outer surface of the electrode element after a predetermined number of activations of the tissue resecting device.

5. The tissue resecting device of claim 4, wherein activation of the tissue resecting device comprises providing RF energy to the electrode element.

6. The tissue resecting device of claim 4, wherein activation of the tissue resecting device comprises axially reciprocating the inner sleeve relative to the outer sleeve.

7. The tissue resecting device of claim 1, wherein the insulative layer is configured to wear away or delaminate from the outer surface of the electrode element after a predetermined total activation time of the tissue resecting device.

8. The tissue resecting device of claim 7, wherein activation of the tissue resecting device comprises providing RF energy to the electrode element.

9. The tissue resecting device of claim 7, wherein activation of the tissue resecting device comprises axially reciprocating the inner sleeve relative to the outer sleeve.

10. A medical device system for resecting tissue, comprising:
   an elongated structure having a longitudinal axis, the elongated structure comprising an outer sleeve with a distal window configured to receive tissue and an inner sleeve configured to move between a proximal position and a distal position relative to the window;
   an electrode element coupled to the inner sleeve and extending distally of the inner sleeve, wherein the electrode element is distinct from the inner sleeve; and
   an insulative layer disposed on an outer surface of the inner sleeve and extending uninterrupted onto an outer surface of the electrode element, wherein the outer surface of the electrode element extends distal of the insulative layer; and
   an RF generator for delivering energy through the electrode element to resect tissue;
   wherein the electrode element serves as an active electrode having a first polarity and the outer sleeve serves as a return electrode having a second polarity opposite the first polarity.

11. The medical device system of claim 10, wherein the insulative layer is configured to wear away or delaminate from the outer surface of the inner sleeve after a predetermined duration of time of using the medical device system.

12. The medical device system of claim 10, wherein the insulative layer is configured to wear away or delaminate from the outer surface of the inner sleeve after a predetermined number of activations of the medical device system.

13. The medical device system of claim 12, wherein activation of the medical device system comprises providing RF energy to the electrode element.

14. The medical device system of claim 12, wherein activation of the medical device system comprises axially reciprocating the inner sleeve relative to the outer sleeve.

15. The medical device system of claim 10, wherein the insulative layer is configured to wear away or delaminate from the outer surface of the inner sleeve after a predetermined total activation time of the medical device system.

16. The medical device system of claim 15, wherein activation of the medical device system comprises providing RF energy to the electrode element.

17. The medical device system of claim 15, wherein activation of the medical device system comprises axially reciprocating the inner sleeve relative to the outer sleeve.

18. A method of resecting tissue, comprising:
   engaging a tissue resecting device with tissue, wherein the tissue resecting device comprises:
      an elongated structure having a longitudinal axis, the elongated structure comprising an outer sleeve with a distal window configured to receive tissue and an inner sleeve configured to move between a proximal position and a distal position relative to the window;
      a tubular electrode element coupled to the inner sleeve and extending distally of the inner sleeve to an open distal end, wherein the electrode element is distinct from the inner sleeve; and
      an insulative layer disposed on an outer surface of the inner sleeve and extending uninterrupted onto an outer surface of the electrode element, wherein the outer surface of the electrode element extends distal of the insulative layer;
   supplying RF energy along an electrical pathway from the electrode element to the outer sleeve as the inner sleeve is axially reciprocated relative to the outer sleeve to generate plasma at a distal edge of the electrode element to resect the tissue received within the distal window.

19. The method of claim 18, wherein the insulative layer is configured to peel back from the outer surface of the inner sleeve after a predetermined number of activations of the tissue resecting device such that when a portion of the outer surface of the inner sleeve is exposed, the electrical pathway from the electrode element to the outer sleeve is altered, thereby rendering the tissue resecting device non-operational.

20. The method of claim 18, wherein the insulative layer is configured to wear away or delaminate from the outer surface of the inner sleeve after a predetermined total activation time of the tissue resecting device such that when a portion of the outer surface of the inner sleeve is exposed, the electrical pathway from the electrode element to the outer sleeve is altered, thereby rendering the tissue resecting device non-operational.

* * * * *